United States Patent [19]

Zukowski

[11] Patent Number: 5,350,690
[45] Date of Patent: Sep. 27, 1994

[54] SUCROSE INDUCIBLE EXPRESSION SYSTEMS

[75] Inventor: Mark M. Zukowski, Thousand Oaks, Calif.

[73] Assignee: Amgen Inc., Thousand Oaks, Calif.

[21] Appl. No.: 876,728

[22] Filed: Apr. 28, 1992

Related U.S. Application Data

[63] Continuation of Ser. No. 659,217, Feb. 22, 1991, abandoned, which is a continuation of Ser. No. 64,933, Jun. 19, 1987, abandoned.

[51] Int. Cl.$^5$ .............. C12N 15/00; C12N 15/03; C12N 15/75
[52] U.S. Cl. .............. 435/252.31; 435/172.3; 435/320.1
[58] Field of Search .............. 435/69.1, 91, 172.1, 435/172.3, 320.1, 71.2, 252.3–252.35, 91.1; 935/29, 41, 74

[56] References Cited

PUBLICATIONS

Zukowski et al, Gene 46: 247 (1986).
Steinmetz et al, Mol. Gen. Genet. 200: 220 (1985).
Aymerich et al, J. Bacteriol. 166: 993 (1986).
Debarouille et al, FEMS Microbiol. Lett. 41: 137 (1987).
Bujard et al, in Promoters, Structure and Function, 1982, Rodriguez et al (ed.), Prager Publishers, New York, NY, pp. 121–140.

*Primary Examiner*—James Martinell
*Attorney, Agent, or Firm*—Richard J. Mazza

[57] ABSTRACT

This disclosure relates to a sucrose inducible expression system. The sucrose inducible expression system comprises a novel plasmid vector having a sacY gene of the sacS locus which binds to a transcription terminator to relieve transcription termination when introduced into a *B. subtilis* host microorganism.

3 Claims, 12 Drawing Sheets

SUCROSE INDUCIBLE EXPRESSION SYSTEMS

This is a divisional of copending application(s) Ser. No. 07/659,217 filed Feb. 22, 1991, abandoned, which in turn is a continuation of Ser. No. 07/064,933, filed Jun. 19, 1987, abandoned.

The present invention relates to novel plasmid vectors which direct and regulate the production of a desired product by expression of heterologous or homologous genes upon sucrose induction of a host microorganism containing such plasmid vectors. The invention further relates to sucrose inducible expression systems containing such plasmids.

BACKGROUND OF THE INVENTION

Levansucrase (sucrose; 2,6-$\beta$-D-fructan 6 $\beta$-D-fructosyltransferase E.C.2.4.1.10) is an extracellular enzyme secreted by *Bacillus subtilis* after induction which occurs following addition of sucrose to the growth medium. Sucrose induces expression of a sacB gene, which encodes levansucrase. Sucrose also induces expression of at least two other structural genes, sacA, which codes for an endocellular sucrose-6-phosphate hydrolase commonly referred to as sucrase, and sacP, which codes for a membrane component of the phosphotransferase system of *B. subtilis* which is involved in sucrose uptake by cells. Genetic and biochemical data concerning uptake and metabolism of sucrose support the view that at least eight loci (sacA, sacB, sacP, sacQ, sacR, sacS, sacT, and sacU) are involved in specific and pleiotropic regulatory mechanisms in the sucrose system of *Bacillus subtilis* 168 [reviewed by Lepesant et al. in Schlessinger, D (Ed.) Microbiology-1976, American Society for Microbiology, Washington, D.C., 1976, pp. 58–69]. Of theses loci, nucleotide sequences have been described for sacA (Fouet et al., Gene 45:221–225, 1986), sacB and sacR (Steinmetz et al., Mol. Gen. Genet. 200:220–228, 1985). The positive regulator gene of the sacS locus is involved in inducible expression of sacB, the gene for levansucrase. The sacB structural gene is preceded by a regulatory region referred to as sacR. The sacR regulator region consists of a constitutive promoter which is followed by a stem-loop region which acts as a rho-independent transcription terminator in the absence of sucrose [Aymerich et al., J. Bacteriol. 166; 993–998, 1986; Shimotsu et al., J. Bacteriol. 168; 380–388, 1986; Zukowski et al., Gene 46:247–255, 1986]. Thus transcription from the constitutive promoter in the sacR regulatory region is arrested by the transcription terminator in the absence of sucrose, mRNA for the sacB structural gene is not synthesized, and levansucrase is not produced. Therefore, in order for sucrose induction to occur, the transcription terminator must be rendered nonfunctional by an anti-terminator.

Regulation of gene expression has been comparatively less characterized in gram-positive bacteria, such as *Bacillus subtilis*, than in the gram-negative enterobacteria, such as *Escherichia coli*. Regulation of gene expression at the level of transcription has been successfully employed in developing several gene expression vectors for efficient, high-level production of foreign proteins in *E. coli*. However, for *B. subtilis* host/vector systems, only two regulated systems have been developed. One system uses *E. coli* lac operator-repressor in *B. subtilis*, resulting in an IPTG-inducible expression of heterologous genes [Yansura & Henner, Proc. Natl. Acad. Sci. U.S.A. 81:439–443, 1984]. This system has limited applications due to the expense associated with the IPTG inducer. The second system is based on thermo-inducible gene expression in *B. subtilis* utilizing transcriptional regulatory elements from the temperate bacteriophage phi-105 [Dhaise et al., Gene 32:181–194, 1984]. This system requires two plasmids in the same host cells, thus increasing the difficulty involved in stably maintaining the host cells and also requires elevated temperatures (~45° C.) for induction, wherein such elevated temperatures may be detrimental to the efficient production of proteins which are sensitive to heat.

SUMMARY OF THE INVENTION

The present invention relates to a sucrose inducible expression system capable of expressing a desired polypeptide in a *B. subtilis* host cell. The invention further relates to novel plasmid vectors which when introduced into a suitable *B. subtilis* host microorganism, enable the resulting expression system to be sucrose inducible. The novel plasmid vectors of the present invention comprise (1) a promoter recognized by *B. subtilis* RNA polymerases, (2) a transcription terminator that is rendered nonfunctional in a host microorganism upon induction with sucrose, (3) a gene encoding the desired polypeptide, and (4) a sacY gene of the sacS locus. The novel sucrose inducible expression systems comprise the above vectors in a suitable *B. subtilis* host microorganism.

The expression system of the present invention is induced upon addition of sucrose to the growth medium and is not subject to temperature control that is, it is not a temperature induced expression system.

DETAILED DESCRIPTION OF THE INVENTION

Figure 1:
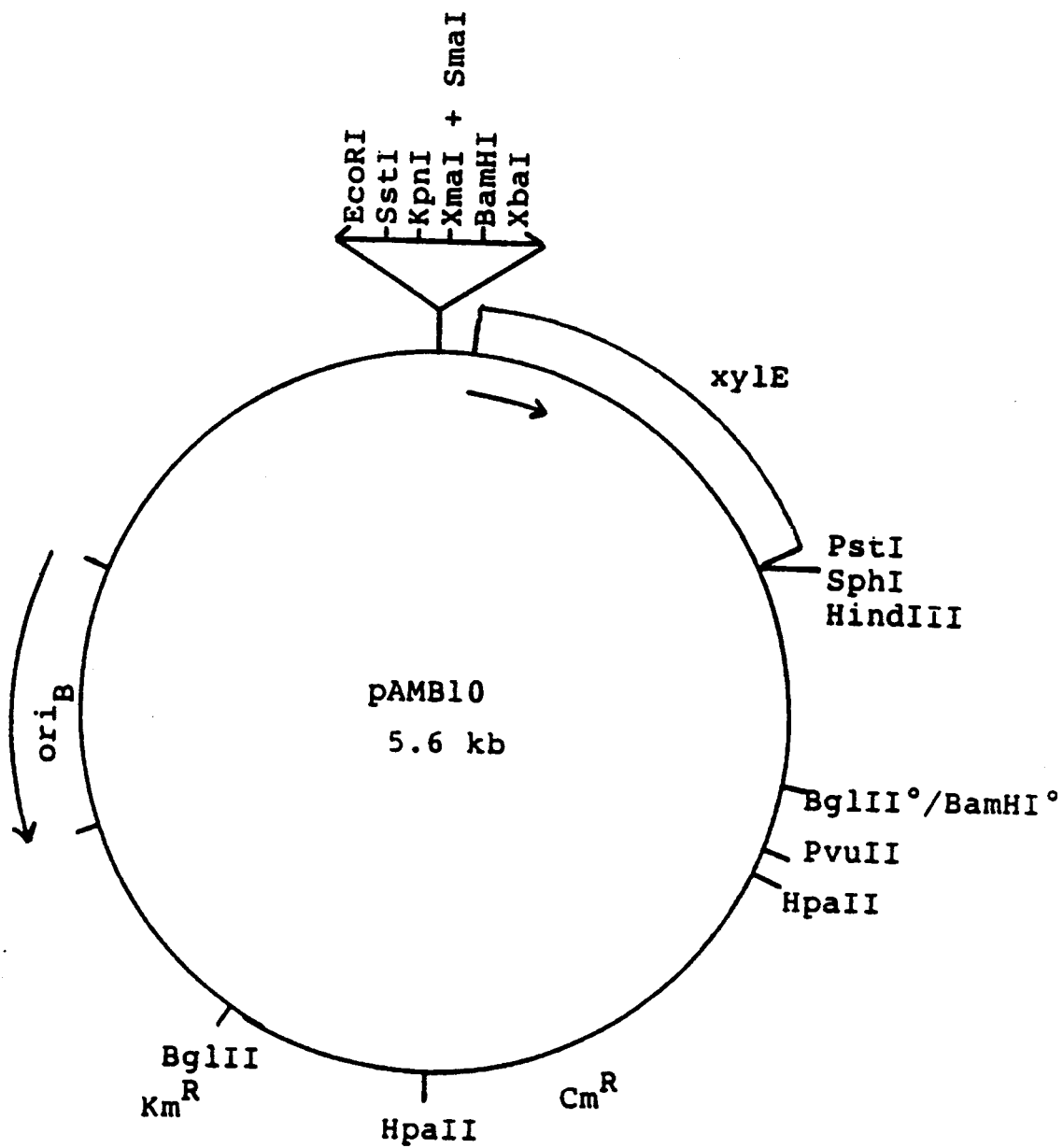
FIG. 1 is a partial restriction map of promoter-probe plasmid pAMB10.

The transportation terminators utilized in the plasmid vectors of the present invention have been also referred to as the "stem-loop region or structure" and function in the absence of sucrose in the growth medium and are recognized by a sacY gene of the sacS locus for induction to occur. Upon induction with sucrose of a host added to the growth medium, the positive regulator gene, sacY, is expressed, the anti-terminator is synthesized, the sacR transcription terminator is rendered nonfunctional, sacB is expressed,

TABLE I

```
                              Met Lys Ile Lys Arg Ile Leu Asn His Asn Ala Ile Val
GGATGAAAGGACAAAAAAGCTATGAAAATTAAAAGAATCTTAAATCATAATGCTATCGTC

Val Lys Asp Gln Asn Glu Glu Lys Ile Leu Leu Gly Ala Gly Ile Ala Phe Asn Leu Lys
GTAAAGGATCAAAATGAAGAGAAGATTCTCTTGGGTGCAGGAATTGCGTTTAACAAAAAG

Lys Asn Asp Ile Val Asp Pro Ser Lys Ile Glu Lys Thr Phe Ile Arg Lys Asp Thr Pro
AAGAATGATATTGTCGATCCGTCAAAAATAGAAAAAACCTTTATCAGAAAAGATACACCT

Asp Tyr Lys Gln Phe Glu Glu Ile Leu Glu Thr Leu Pro Glu Asp His Ile Gln Ile Ser
GACTATAAGCAGTTCGAAGAGATTTTAGAAACATTGCCTGAAGACCACATTCAGATTTCT

Glu Gln Ile Ile Ser His Ala Glu Lys Glu Leu Asn Ile Lys Ile Asn Glu Arg Ile His
GAGCAAATTATCTCTCATGCCGAAAAAGAGCTGAACATCAAAATCAACGAGCGCATTCAT

Val Ala Phe Ser Asp His Leu Ser Phe Ala Ile Glu Arg Leu Ser Asn Gly Met Val Ile
GTCGCTTTTTCAGACCATCTTTCTTTTGCAATTGAACGCCTGAGCAATGGGATGGTTATC

Lys Asn Pro Leu Leu Asn Glu Ile Lys Val Leu Tyr Pro Lys Glu Phe Gln Ile Gly Leu
AAAAATCCGCTGCTGAATGAAATCAAAGTCCTTTATCCAAAGGAGTTCCAGATCGGCTTA

Trp Ala Arg Ala Leu Ile Lys Asp Lys Leu Gly Ile His Ile Pro Asp Asp Glu Ile Gly
TGGGCCAGAGCACTGATTAAAGATAAACTGGGGATTCACATTCCTGATGATGAAATCGGC

Asn Ile Ala Met His Ile His Thr Ala Arg Asn Asn Ala Gly Asp Met Thr Gln Thr Leu
AATATCGCCATGCATATCCACACAGCAAGAAACAATGCCGGCGATATGACACAAACGCTT

Asp Ile Thr Thr Met Ile Arg Asp Ile Ile Glu Ile Ile Glu Ile Gln Leu Ser Ile Asn
GATATTACAACAATGATCCGTGATATTATCGAGATTATCGAAATTCAACTGTCTATTAAT

Ile Val Glu Asp Thr Ile Ser Tyr Glu Arg Leu Val Thr His Leu Arg Phe Ala Ile Gln
ATCGTTGAAGATACCATCTCTTATGAAAGGCTCGTGACCCATCTCCGCTTTGCCATTCAG

His Ile Lys Ala Gly Glu Ser Ile Tyr Glu Leu Asp Ala Glu Met Ile Asp Ile Ile Lys
CATATCAAAGCAGGCGAATCCATTTACGAGCTGGACGCAGAAATGATTGACATCATTAAA

Glu Lys Phe Lys Asp Ala Phe Leu Cys Ala Leu Ser Ile Gly Thr Phe Val Lys Lys Glu
GAGAAGTTTAAGGATGCCTTCCTGTGTGCCCTAAGCATCGGCACCTTTGTGAAGAAGGAA

Tyr Gly Phe Glu Phe Pro Glu Lys Glu Leu Cys Tyr Ile Ala Met His Ile Gln Arg Phe
TACGGCTTTGAGTTTCCTGAAAAAGAATTGTGCTACATCGCCATGCATATTCAGCGGTTC

Tyr Gln Arg Ser Val Ala Arg End
TACCAACGGTCAGTCGCACGCTGAGACAAACAAAAAACGCTTTTGATCATCTCAAAAGCG

TTTTTTTCATCTGATTTATTG
``` microorganism containing a vector having such a transcription terminator, the transcription terminator is rendered nonfunctional, thus enabling expression of the desired polypeptide product.

The gene encoding the desired polypeptide product include homologous or heterologous genes of Bacillus species. The structure and properties of such genes are readily ascertained by one of ordinary skill in the art. Examples of homologous genes are those derived from the *B. subtilis* chromosome, such as those which code for alkaline protease, neutral protease, α-amylase, β-glucanase, etc. Examples of heterologous genes are bovine somatotropin, porcine somatotropin, human granulocyte colony stimulating factor and human interferons.

As used herein, the term "sacY" refers to a gene in the sacS locus the product of which binds to the sacR stem-loop region to relieve transcription termination. The nucleotide sequence of a sacY positive regulator gene utilized herein and the deduced amino acid sequence of the polypeptide encoded thereby is represented in Table I. In the presence of sucrose, the sacR transcription terminator is rendered nonfunctional by an anti-terminator encoded by sacY. When sucrose is and levansucrase is secreted into the surrounding growth medium. A negative regulatory region, sacX, presumably functions by preventing synthesis or function of sacY or its gene product in the absence of sucrose. However, sacX has not been completely genetically or biochemically characterized.

The term "sucrose induction" refers to the expression of a polypeptide from a host microorganism upon addition of sucrose to the growth medium.

A preferred embodiment of the present invention employs sacY in multiple copies thus resulting in greater level of expression of the desired polypeptide product. A preferred embodiment employs a sacR transcription terminator as the transcription terminator.

In accordance with the present invention, a fragment of *B. subtilis* chromosomal DNA containing the sacR regulatory region of sacB is cloned on a promoter-probe plasmid containing a gene encoding the desired polypeptide to be expressed and the resulting plasmid is introduced into a *B. subtilis* host cell. Sucrose-induction of the host cells containing the plasmid results in expression of the desired polypeptide. When a sacY positive regulator gene is also cloned on the promoter-probe plasmid containing sacR, sucrose-induction of the resulting host cells harboring the sacY containing plasmid results in expression of the desired polypeptide at greater levels than obtained in host cells not containing the sacY gene on the plasmid. The presence of the product of the sacY positive regulator gene, a transcription anti-terminator, has a stimulatory effect on gene expression which results in higher quantities of the desired product being produced after induction by sucrose.

As previously noted, the sucrose inducible expression systems are not temperature dependent in that the growth medium must be maintained at a particular temperature in order for induction to occur. In accordance with the present invention, the growth medium is preferably maintained within a temperature range of from about 22° C. to about 37° C. and the temperature has no effect upon induction.

Another embodiment of the present invention involves replacement of the promoter in the sacR regulatory gene with a strong constitutive promoter which does not depend on the presence of the sacU$^h$ mutation in Bacillus host cells for high-level expression. Such promoters include, for example, a synthetic consensus T5 promoter. The nucleotide sequence of a consensus T5 promoter and sacR stem-loop region are represented in Table II. The "−35" and "−10" promoter sequences involved in RNA polymerase recognition are indicated. Arrows depict the stem of the stem-loop region which forms due to pairing of complementary bases. The EcoRI (GAATTC) and XbaI (TCTAGA) restriction endonuclease sites are indicated. The strong constitutive promoter is placed upstream of the subfragment of sacR which contains the stem-loop (transcription terminator) sequence. The resulting plasmid is introduced into an appropriate host microorganism. Sucrose-induction of the host cell results in expression of the desired product. When a sacY positive regulator gene is cloned on plasmids containing such strong constitutive promoters, sucrose induced expression results in increased levels of expression of the desired protein compared to expression levels in similar cells lacking a sacY positive regulator gene.

For the purposes of illustration in the following Examples, catechol 2,3-dioxygenase, encoded for by the indicator xylE gene, is utilized as the protein product of interest. Because the xylE gene encodes catechol 2,3-dioxygenase, it is useful for detecting promoters in a variety of organisms.

EXAMPLE 1

Construction of Promoter-Probe Plasmids pAMB10 and pAMB11

Plasmid pTG402 (Northern Regional Research Laboratories, United States Department of Agriculture, Peoria, Ill., strain number NRRL B-15264) containing a xylE gene was partially digested with the RsaI restriction endonuclease. The resulting fragment mixture was ligated to M13 mp18 (available from Bethesda Research Laboratories, Gaithersburg, Md.) which had been previously digested with HincII. The ligation product mixture was transformed into *E. coli* JM103 (available from Pharmacia, Inc., Piscataway, N.J.) in accordance with the procedures of Mandel et al., J. Mol Biol. 53: 154, 1970. The resulting bacteriophage plaques were sprayed with 0.5M catechol to detect the functional expression of xylE gene.

Figure 10:
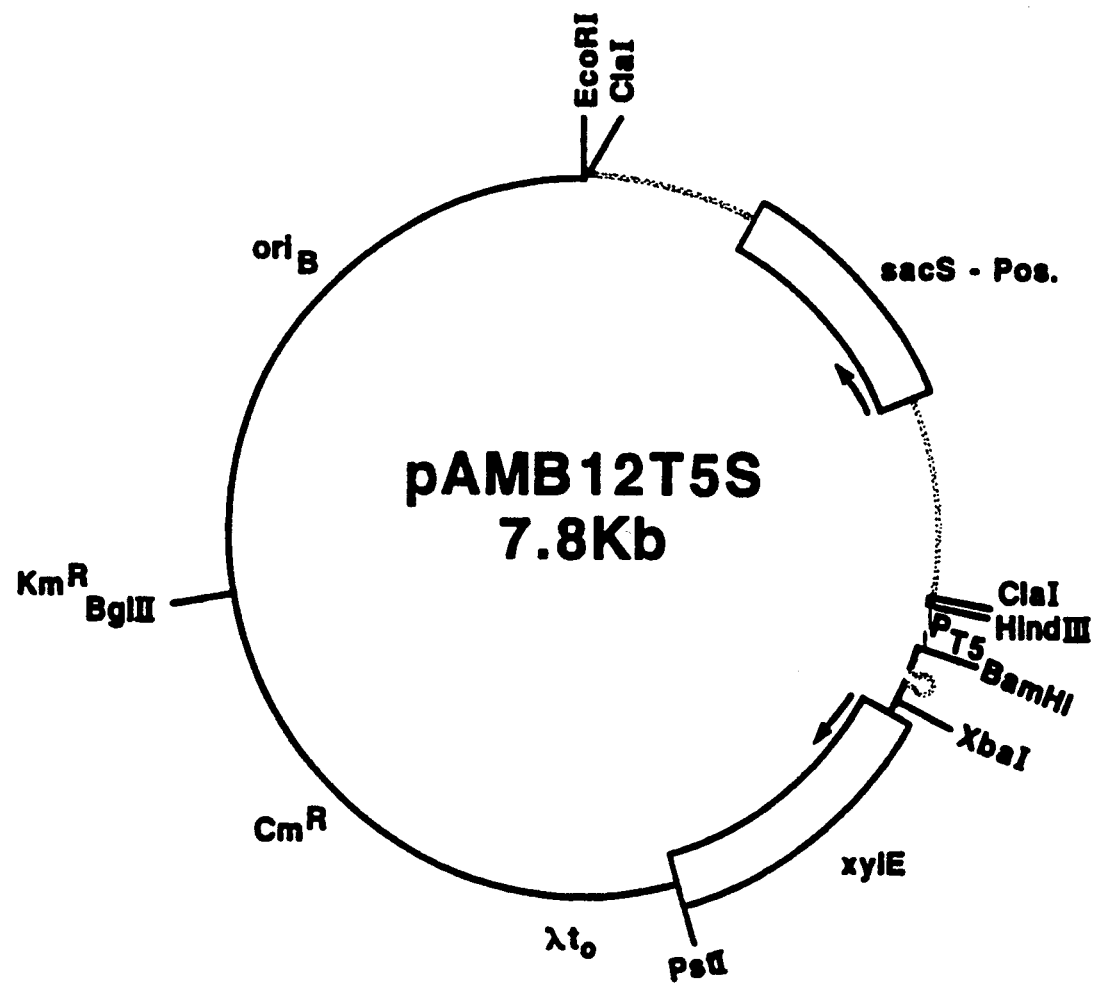
FIG. 10 is a partial restriction map of pAMB12T5S.

The xylE gene was then transferred as a 1.6 kilobase pair (kb) EcORI to BglII fragment from M13 mp18 to a Bacillus cloning vector pBD64 (available from the Bacillus Genetic Stock Center, the Ohio State University, Columbus, Ohio) which had been previously digested with EcoRI and BamHl . The resulting 5.6 kb plasmid, pAMB10, contains the polylinker sequence of M13 mp18 (EcoRI, SstI, XmaI, SmaI, BamHl, and XbaI) upstream of the xylE gene which is followed by 665 bp of M13 mp18 DNA (FIG. 10). Plasmid pAMB-1was the vector used for the construction of plasmid pA51 as described in Example 2.

For construction of plasmid pAMB11, the xylE gene was first transferred from the M13 mp18 cloning vector as a 1.0 kb EcoRI to PstI fragment to an *E. coli/B. subtilis* plasmid pHV33 (available from the American Type Culture collection as ATCC 39217). The pHV33 plasmid had been previously digested with EcoRI and PstI enabling the xylE-containing fragment, when ligated in this region, to inactivate a gene encoding ampicillin resistance to *E. coli* host cells. The resulting plasmid, pAMB21, contains a functional xylE gene in *E. coli* host cells, but requires the addition of a promoter for xylE to be expressed in *B. subtilis* host cells. *E. coli* cells harboring pAMB21 are resistant to tetracycline (Tc$^R$; 15 μg/ml) and chloramphenicol (Cm$^R$; 20 μg/ml) while

TABLE II

```
    EcoRI
  1 GAATTCTCAT GTTTTGACAG CTTATCATCG ATAAGCTTCA TAAAAATTTT
            −35                −10
 51 AGTTGCTTAA TGCTAAAATT CTTGATATAA TATTCTCAAT TGTGAGCGGA

101 TAACAATTTA TCGATAAGGA GGATCCTCTA GCGAAAAGTA AATCGCGCGG
                                                       ────────>
151 GTTTGTTACT GATAAAGCAG GCAAGACCTA AAATGTGTAA AGGGCAAAGT
    <────      <─────

201 GTATACTTTG GCGTCACCCC TTACATATTT TAGGTCTTTT TTTATTGTGC

251 GTAACTAACT TGCCATCTTC AAACAGGAGG GCTGGAAGAA GCAGACCGCT
            XbaI
301 AACACAGTCT AGA
```

*B. subtilis* cells harboring pAMB21 are resistant only to chloramphenicol (5 μg/ml).

The transcription termination sequence $t_o$ of bacteriophage lambda was transferred from plasmid pCFM936 (available from the American Type Culture collection as ATCC 53413) (on a 400 bp PstI to BglII fragment) to the unique PstI site of pAMB21. A synthetic nucleotide having the sequence, 5' GATCTGCA 3' was constructed by the phosphite chemistry method of Beaucage et al., (Tetrahedron Letters 22: 1859–1862, 1981) to join the BglII extremity of the λ to fragment to the PstI site of the vector pAMB21. The resulting plasmid was designated pAMB22 and has properties identical to pAMB21 except for the inclusion of the transcription terminator. The resulting pAMB22 plasmid is useful for detecting strong promoters that are functional in *B. subtilis.*

Figure 2:
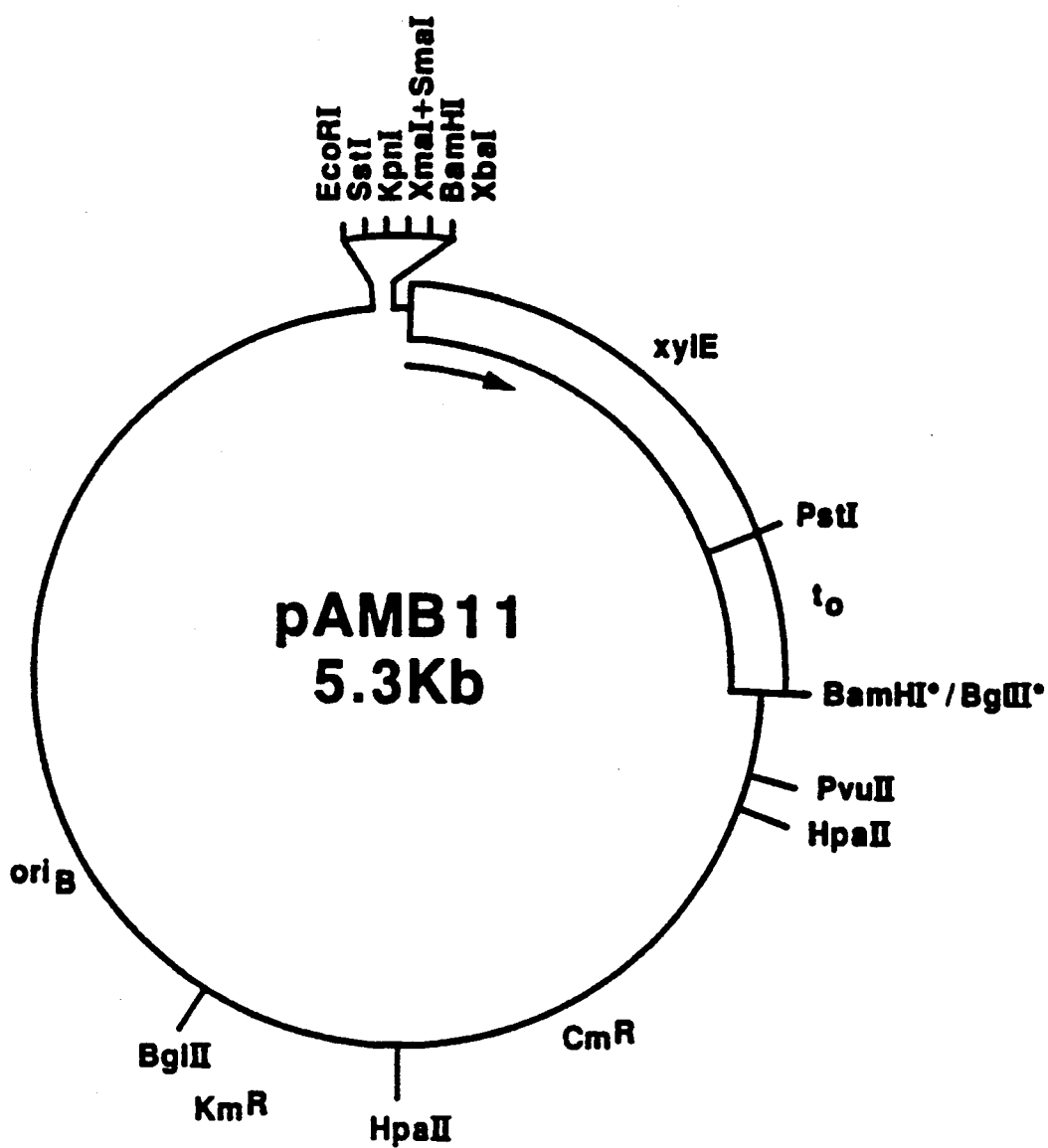
FIG. 2 is a partial restriction map of promoter-probe plasmid pAMB11.
Figure 3:
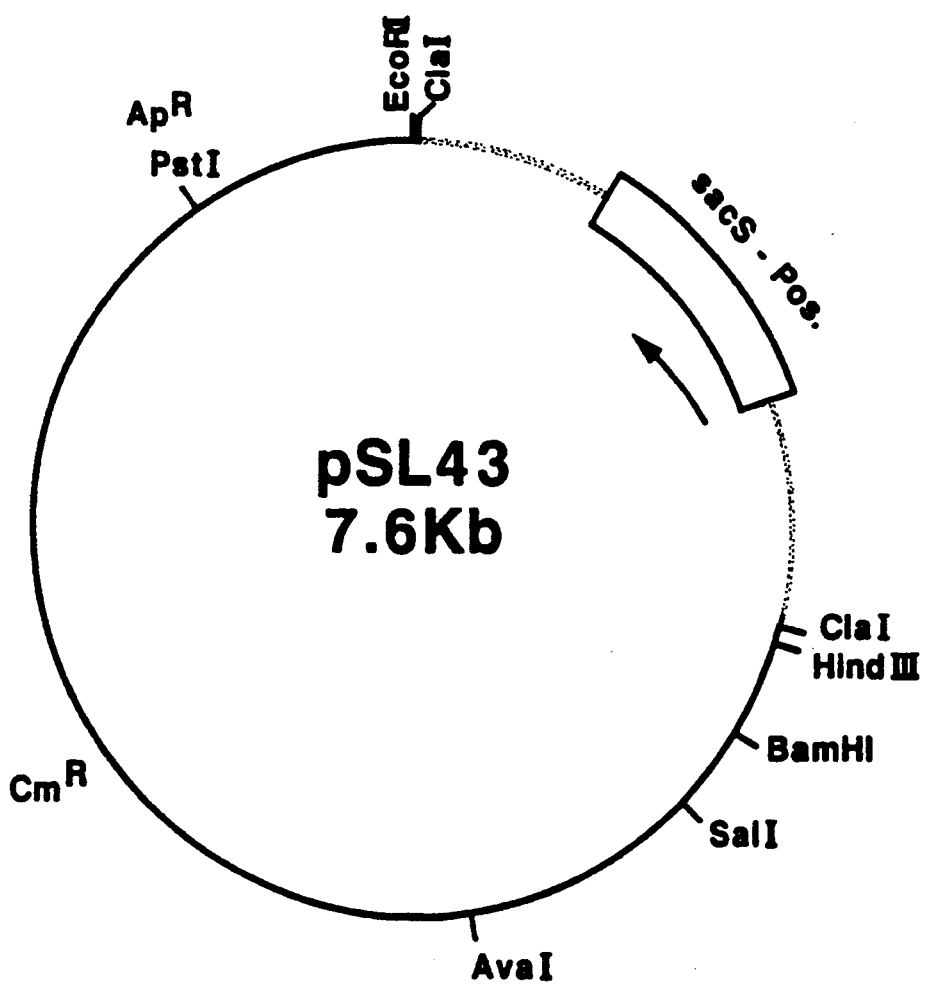
FIG. 3 is a partial restriction map of pSL43.
Figure 4:
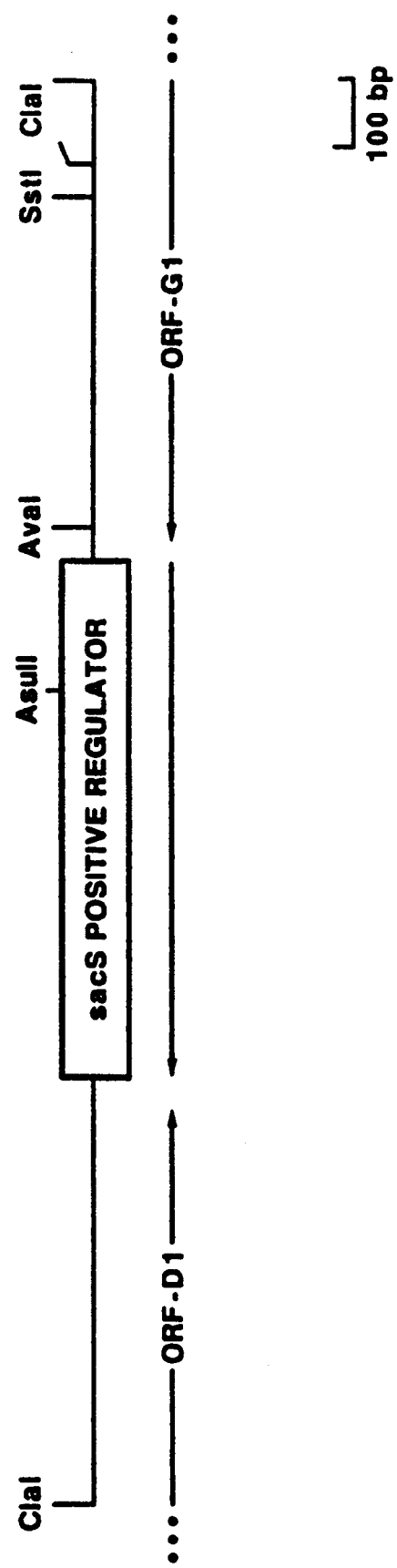
FIG. 4 is a partial restriction map of a 2.15 kb fragment of DNA from pSL43 that contains a major portion of the sacS locus and consists of the complete sequence for the sacS positive regulator gene (sacY) and partial sequences for open reading frame G1 (the sacX negative regulator gene) and open reading frame D1 (unrelated to the sacS locus).

A 1.4 kb EcoRI to BglII fragment of DNA from pAMB22 that contains xylE and λ to was transferred to plasmid pBD64 which had been previously digested with EcoRI and BamHI . The resulting 5.3 kb plasmid, pAMB11, contains the polylinker sequence of M13 mp18 (EcoRI, SstI, XmaI, SmaI, BamHI, XbaI) upstream of the xylE gene which is followed by the λ to transcription terminator (Zukowski et al., supra) and is illustrated in FIG. 2. The pAMB11 plasmid is capable of replicating in *B. subtilis* where it confers upon host cells resistance to chloramphenicol (5 μg/ml) and/or kanamycin (Km$^R$; 5 μg/ml). The pAMB11 plasmid is useful for detecting strong promoters that are functional in *B. subtilis.*

EXAMPLE 2

Construction of Plasmid pA51

Chromosomal DNA from *B. subtilis* strain BD224 (available from the Bacillus Genetic Stock Center as strain #BGSC 1A46) was isolated as follows.

A 100 ml culture of cells in Penassay Broth (Difco; Antibiotic Medium #3) was grown at 37° C. overnight with agitation. The culture was centrifuged and the supernatant was discarded and the cell pellet was resuspended in 10 ml TES buffer (10mM Tris-HCl; pH 8.0; 1 mM EDTA; 5 mM NaCl). Lysozyme was added to a final concentration of 0.5 mg/ml, and the suspension was incubated at 37° C. for 30 min. Sodium dodecyl sulfate was added to a 1% final concentration to lyse the cells completely. RNaseA was added to a 20 μg/ml final concentration and the cell extract was heated at 37° C. for 30 min. Proteinase K was added to a 50 μg/ml final concentration and the cell extract for heated again at 37° C. for an additional 60 min. The cell extract was then extracted twice with equal volumes of phenol. Ice cold ethanol (2 volumes) was added to the solution, whereupon chromosomal DNA precipitated. The mixture was centrifuged and the liquid phase was discarded and the remaining DNA pellet was air-dried. The DNA pellet was resuspended in 500 μl TE buffer (10 mM Tris-HCl, pH 8.0; 0.1 mM EDTA). BD224 chromosomal DNA was digested with HindIII and the resulting fragments were resolved on a 1% low melting temperature agarose gel by electrophoresis. A gel section containing fragments in a 3.0 to 4.4 kb size range was excised from the gel and DNA fragments were separated from the gel. The DNA fragments were ligated to plasmid pBR322 (available from Bethesda Research Laboratories) which was previously digested with HindIII. The ligation mixture was transformed into *E. coli* strain C600 (American Type Culture Collection #ATCC 23724) in accordance with the procedure of Mandel et al., J. Mol. Biol. 53: 154, 1970. Because the unique HindIII site of pBR322 resides within the promoter sequence of the tet gene which confers tetracycline resistance (Tc$^R$) upon host cells, insertion of DNA into this site would, in most cases, leave plasmid-bearing host cells sensitive to tetracycline but resistant to ampicillin (Ap$^R$) due to the presence of the β-lactamase gene. Therefore, Ap$^R$ cells were screened for Tc sensitivity as an indication that *B. subtilis* BD224 chromosomal DNA was inserted in the plasmid cloning vector. Ap$^R$Tc$^S$ colonies were propagated on fresh growth plates containing 50 μg/ml ampicillin, then transferred to nitrocellulose filters and processed by a colony hybridization procedure [Grunstein et al., Proc. Natl. Acad. Sci. USA 72: 3961, 1975].

A probe was used to screen colonies which harbored the desired fragment of DNA which carried the genetic regulatory region known as sacR and a major portion of the gene controlled by sacR which is known as sacB (encodes levansucrase). The probe (synthesized by the phosphite chemistry method of Beaucage et al., Tetrahedron Letters 22: 1859–1862, 1981) had the nucleotide sequence:

5' CAGCAGTGCGGTAGTAAAGG 3' which corresponds to DNA which will hybridize to the signal peptide region of sacB coding for amino acids noted as −10 through −16 in the publication of Fouet et al., Biochem Biophys. Res. Comm. 119: 795–800, 1984. One positive colony, when examined for plasmid DNA content in accordance with the procedures described by Birnboin and Doly , Nucleic Acids Res. 7: 1513–1523, 1979. was found to harbor the pBR322 cloning vector with a 3.15 kb insert of BD224 chromosomal DNA. The fragment conformed to the description of Gay et al., (J. Bacteriol 153: 1424–1431, 1983) as determined by restriction endonuclease analysis and DNA sequencing.

Figure 5:
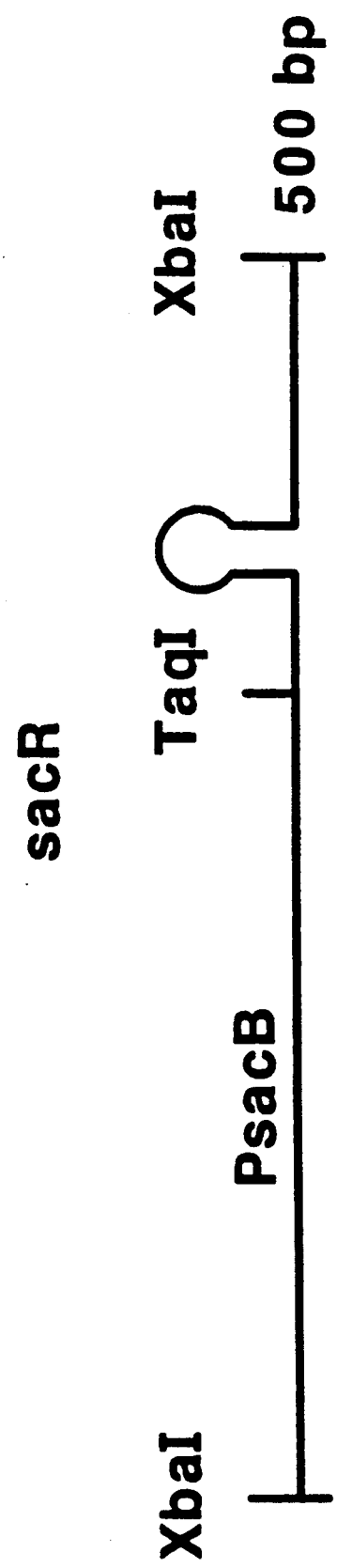
FIG. 5 illustrates a the 500 bp RsaI fragment (extremities converted to XbaI) of *B. subtilis* chromosomal DNA that wholly contains the sacR regulatory region wherein the sacR region consists of a constitutive promoter (P sacB) followed by a transcription terminator (stem-loop region).
Figure 6:
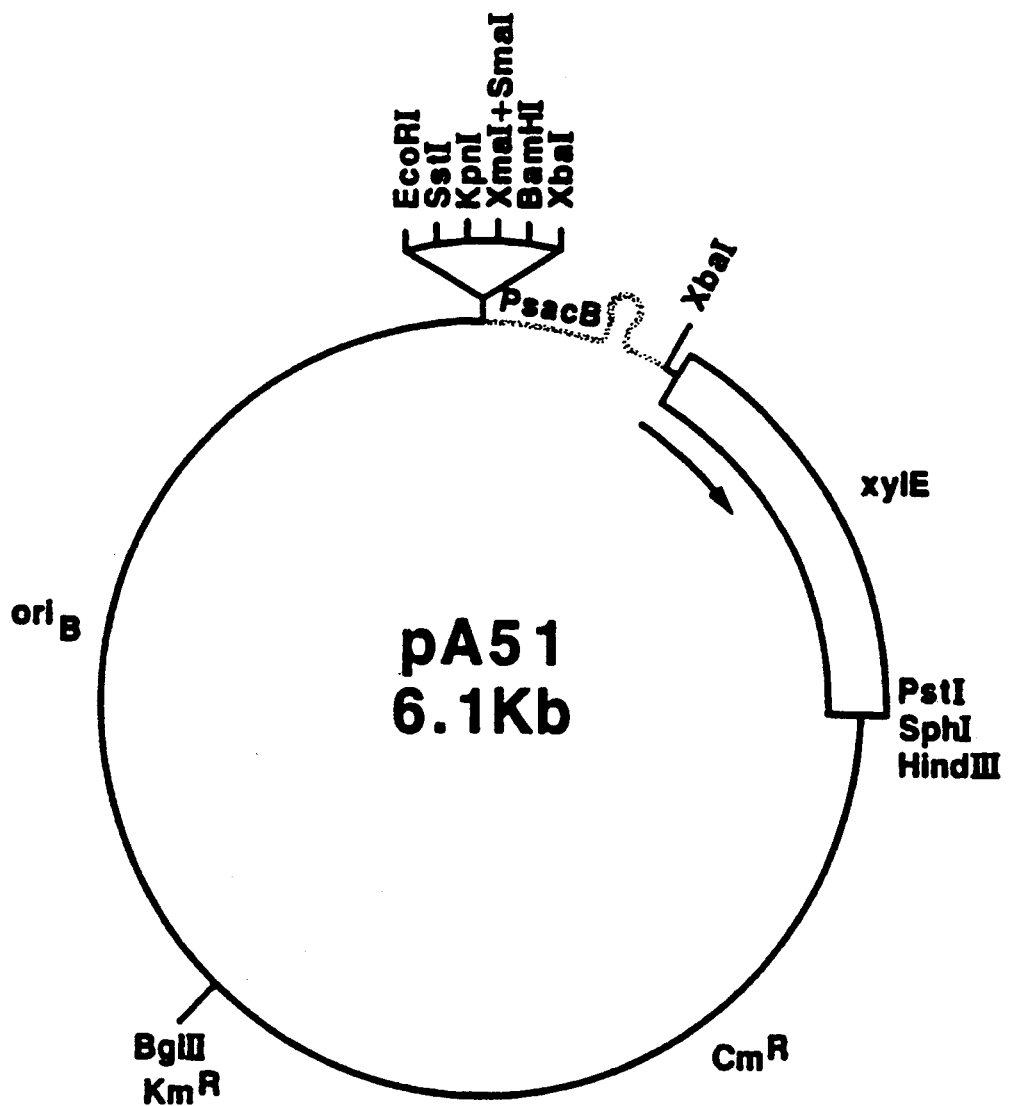
FIG. 6 is a partial restriction map of pA51.

A 500 bp RsaI subfragment of the 3.15 kb insert which carries the sacR sequence (Zukowski et al., supra) was then transferred to plasmid pAMB22 which was previously digested with XbaI and end-filled with complementary nucleotides by using the Klenow (large) fragment of *E. coli* DNA polymerase I according to the method described by Maniatis et al., Molecular Cloning, Cold Spring Harbor Laboratory Press, pp. 113–114, 1982. The procedure permitted the re-isolation of sacR on a 500 bp XbaI fragment from the pAMB22 cloning vector. This 500 bp XbaI fragment (FIG. 5) was then transferred from the pAMB22 cloning vector to the XbaI site of pAMB10. The resulting plasmid, designated pA51 (FIG. 6) contains the sacR regulatory region of *B. subtilis* chromosomal DNA and allows for inducible expression of the xylE indicator gene on the same plasmid.

EXAMPLE 3

Construction of Plasmid pA51S

Plasmid pSL43 (American Type Culture Collection #ATCC 67444) was digested with ClaI yielding a 2.15 kb fragment of *B. subtilis* DNA of pSL43 which has the nucleotide sequence that codes for the sacS positive regulator gene as well as 5-prime and 3-prime flanking sequences. The 2.15 kb ClaI fragment was sequenced in its entirety using the dideoxy chain termination method [Sanger et al., J. Mol. Biol. 143: 161–178, 1980]. The coding sequence for the sacS positive regulator gene sacY was identified as being the only complete open reading frame sequence on the 2.15 kb fragment.

Figure 7:
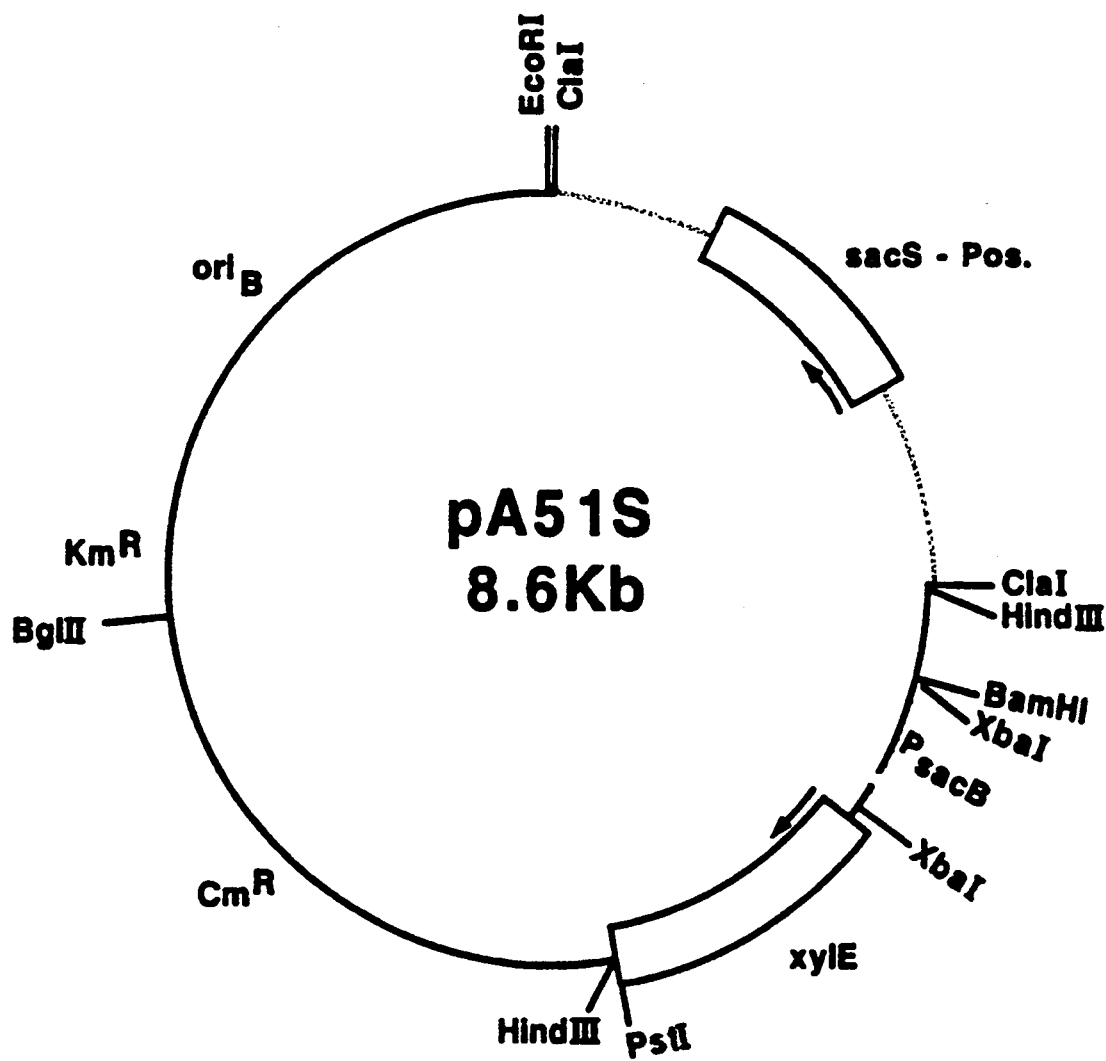
FIG. 7 is a partial restriction map of pA51S.
Figure 8:
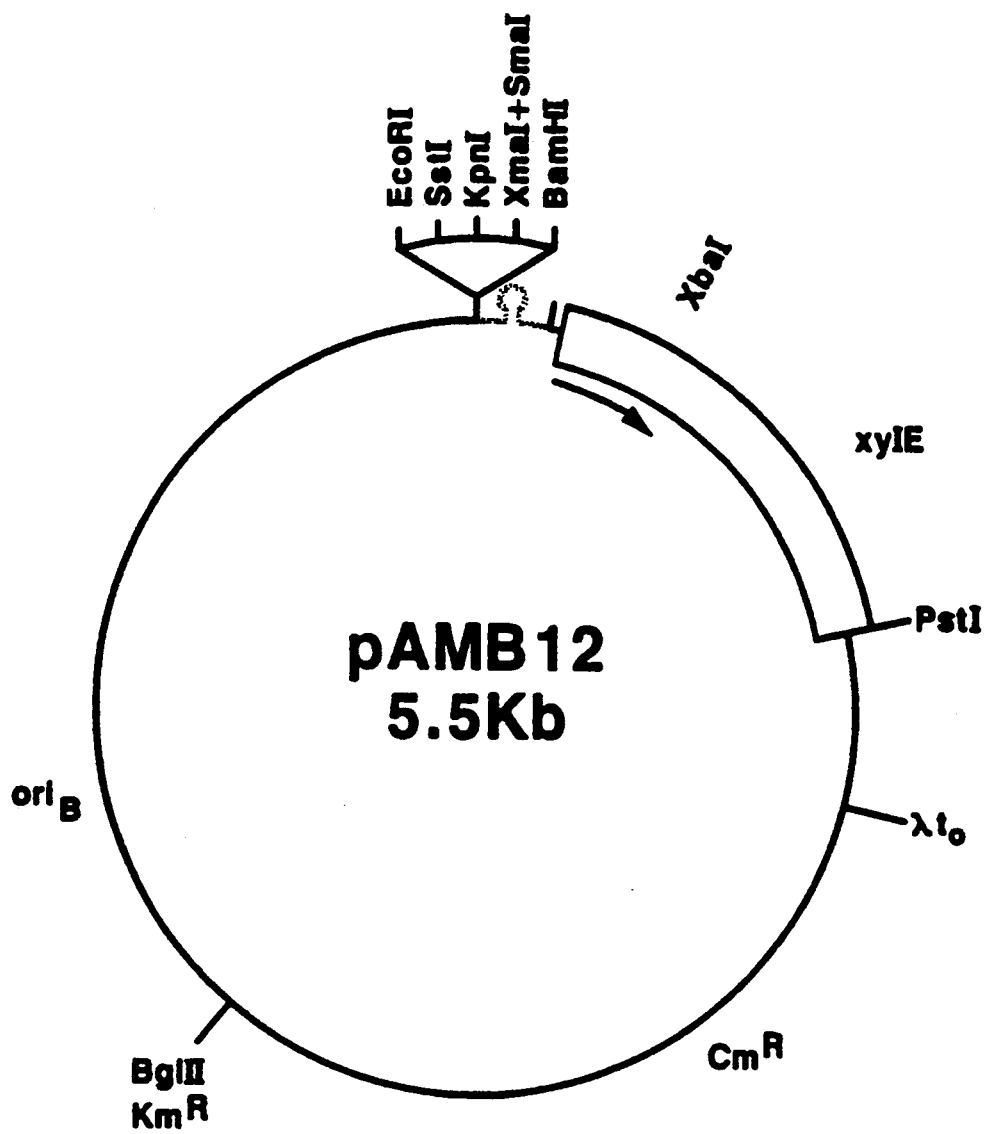
FIG. 8 is a partial restriction map of pAMB12.

Plasmid pSL43 was digested with EcoRI and BamHI in combination. The resulting 2.15 kb fragment containing the sacS positive regulator gene was transferred to pA51 which had been previously digested with EcoRI and BamHI. The resulting plasmid was designated pA51S (American Type Culture Collection, Rockville, Md., ATCC accession no. 68345) (FIG. 7) and allows for inducible expression of the xylE gene.

EXAMPLE 4

Construction of Plasmid pAMB12T5

The 500 bp fragment of *B. subtilis* chromosomal DNA that contains the sacR regulatory region carries a TaqI restriction endonuclease site in a position downstream of the promoter for sacB gene expression and upstream of a stem-loop region which has been shown to be involved in the induction process [Aymerich et al., 1986, supra; Shimotsu et al., 1986, supra; Zukowski et al., 1986, supra].

Digestion of the 500 bp sacR-containing fragment with TaqI separates sacR into its two components: a 325 bp subfragment which carries the promoter and a 175 bp subfragment which carries the stem-loop region involved in the induction process. The 175 bp subfragment was transferred to plasmid pAMB22 as described by Zukowski et al., 1986, supra, to form plasmid pAMB24.

A 1.6 kb EcoRI to PStI fragment of DNA from pAMB24 was ligated to plasmid pAMB11 which had been previously digested with EcoRI and PstI. Ligation products were introduced into *B. subtilis* strain MI112 (Bacillus Genetic Stock Center #BGSC 1A423) by transformation of protoplasts [Chang and Cohen, Mol. Gen. Genet. 168: 111–115, 1979]. The resulting plasmid, designated pAMB12, carries restriction endonuclease sites for EcoRI, PstI, KpnI, SmaI, and BamHI which are followed by the 175 bp fragment of *B. subtilis* DNA carrying the sacR stem-loop region, and this is followed by the xylE indicator gene. Because a promoter sequence is not present in the polylinker (EcoRI to BamHI) region of pAMB12, xylE is not expressed in *B. subtilis* host cells.

Figure 9:
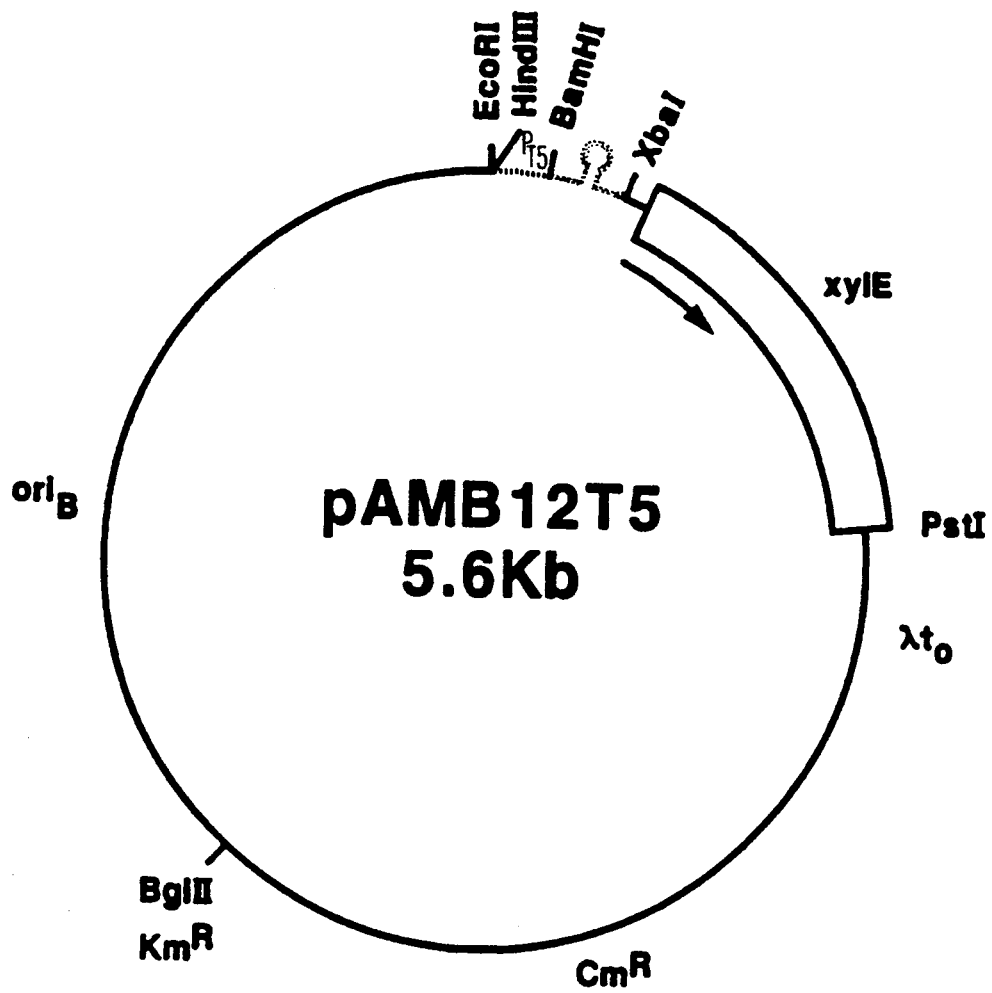
FIG. 9 is a partial restriction map of pAMB12T5.

A bacteriophage consensus T5 promoter comprising the −10 region of P26 and the −35 to −50 regions of P25, P26 and P28 [Bujard et al., in Rodriguez, R. and Chamberlin, M. (Eds) Promoters; Structure and Function, Praiger, N.Y., pp. 121–140, 1982] and followed by a lac operator sequence, was synthesized by the phophoramidite chemistry method of Beaucage et al., supra, 1981. The 88 bp HindIII to BamHI fragment was transferred to the large segment of plasmid pBR322 which resulted after digestion with HindIII and BamHI in combination. The synthetic consensus T5 promoter was then transferred to pAMB12 on a 117 bp EcoRI to BamHI fragment. The resulting plasmid was designated pAMB12T5 (American Type Culture Collection, ATCC accession no. 68344) (FIG. 9), and allowed for sucrose inducible expression of the xylE gene as described in Example 7. The nucleotide sequence of the EcoRI to XbaI fragment of pAMB12T5 is presented in Table II.

EXAMPLE 5

Construction of Plasmid pAMB12T5S

Plasmid pSL43 was digested with EcoRI and HindIII in combination. The resulting 2.2 kb fragment containing the sacS positive regulator gene sacY was transferred to pAMB12T5 which had been previously digested with EcoRI and HindIII. The resulting plasmid was designated pAMB12T5S (FIG. 10), and allows for inducible expression of the xylE gene.

EXAMPLE 6

Inducible Expression in GM120/pA51 and GM120/pA51S

Plasmids pA51 and pA51S were separately introduced into *B. subtilis* GM120 sacA321 Δ(sacR-B)23 sacU$^h$32 (ATCC 53631) by transformation of protoplasts [Chang et al., Mol. Gen. Genet. 168: 111–115, 1979].

*B. subtilis* strains GM120/pA51 and GM120/pA51S were cultured individually in Brain Heart Infusion broth (BHI; Defco Laboratories) supplemented with 10 µg/ml chloramphenicol. The cultures were propagated at 37° C., with agitation for a period of about 15–16 hours. The cultures were diluted in fresh BHI supplemented with chloramphenicol until the optical density at 660 nm was typically in the range of 0.025 to 0.050 O.D. units. The cells were grown for 1 to 2 generations until the culture had an optical density of 0.10 units. The culture was equally divided into two flasks: one received no inducer while the other was supplemented with sucrose at a 100 mM final concentration. The cell cultures continued to grow at 37° C. with shaking. At various time intervals, 1 ml samples of culture were removed to determine C23O specific activity, an indication of xylE gene expression.

To determine C23O specific activity, 1 ml of cell culture was centrifuged in an Eppendorf Microfuge for 2 min. The supernatant was discarded and the cell pellet was then washed with 0.5 ml of 20 mM phosphate buffer, pH 7.2. The cell suspension was centrifuged as before, the supernatant discarded, and the pellet resuspended in 0.5 ml of 0.1M phosphate buffer—10% acetone—1 mg/ml lysozyme. After incubation at 37° C. for 10 min., the cell suspension was cooled on ice. The cells were disrupted by sonication for 15 sec. in 3×5 sec. intervals with thorough cooling between intervals. Cellular extracts were centrifuged for 15 min. at 4° C. to remove debris. The supernatant was saved and the pellet discarded.

C23O activities were determined as described by Sala-Trepat and Evans, Eur. J. Biochem. 20: 400–413, 1971. Protein concentrations were determined by the Bradford method, using the reagents and protocol of the supplier. One milliunit of enzyme activity corresponds to the formation at 22° C. of 1 nmol of 2-hydroxymuconic semialdehyde per min.

Figure 11:
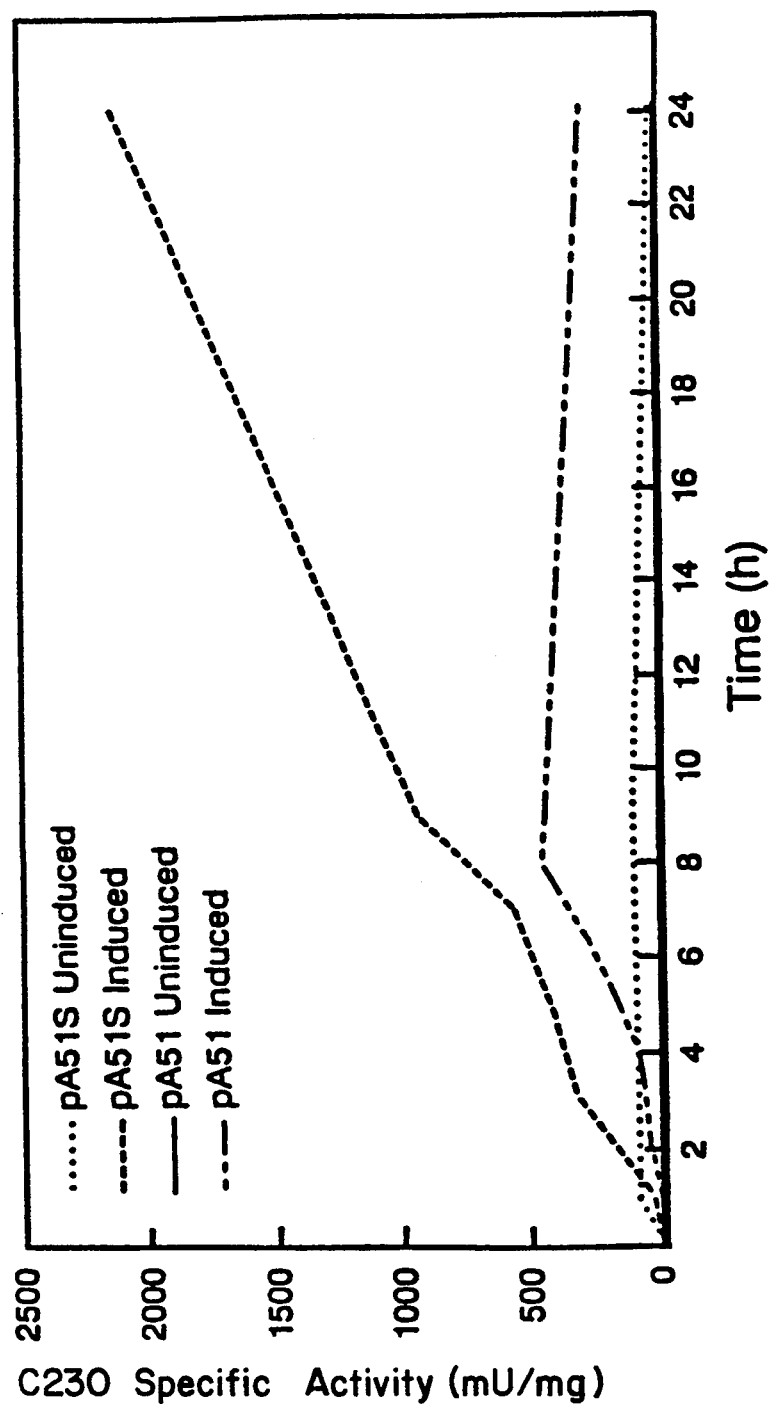
FIG. 11 compares expression of xylE by pA51 and pa51S in *B. subtilis* GM120 host cells.

Whereas no C23O enzyme activity was detected in GM120/pA51 when no inducer was added, C23O was produced from 2 to 24 hours after adding the sucrose inducer (FIG. 11). Maximal C23O activity was observed 8 hours after the addition of sucrose.

In a parallel series of experiments, little C23O enzyme activity was detected in GM120/pA51S when no inducer was added. When the culture was induced with sucrose, C23O was produced at levels superior to those observed in the GM120/pA51 culture which was likewise induced (FIG. 11). Thus the presence of the sacY positive regulator gene on the pA51S plasmid positively affected the amount of C23O produced by the *B. subtilis* host cells.

EXAMPLE 7

Inducible Expression in GM120/pAMB12T5 and GM120/pAMB12T5S

Plasmids pAMB12T5 and pAMB12T5S were introduced separately into *B. subtilis* GM120 sacA321

Δ(sacR-B)23 sacU$^h$32 as described in Example 6 to yield strains GM120/pAMB12T5 and GM120/pAMB12T5S respectively.

*B. subtilis* strains GM120/pAMB12TS and GM120/pAMB12T5S were cultured individually in BHI broth and cell extracts for determining C230 specific activities were prepared as described in Example 6.

Figure 12:
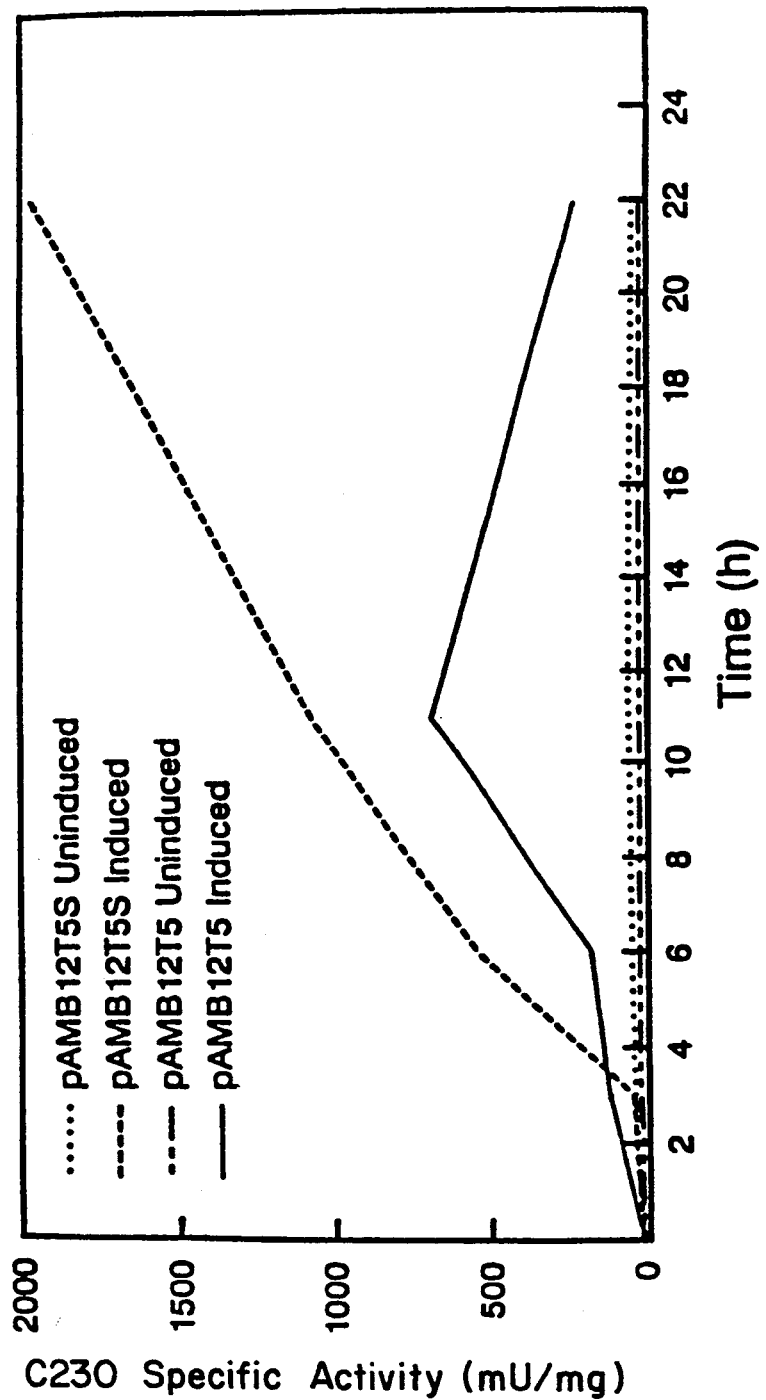
FIG. 12 compares expression of xylE by pAMB12T5 and pAMB12T5S in *B. subtilis* GM120 host cells.

As illustrated in FIG. 12, very little enzyme activity was detected in GM120/pAMB12TS when no inducer was added, C230 was produced 3–25 hours after adding the sucrose inducer. Maximal C230 enzyme activity was observed 11 hours after addition of sucrose. In a parallel series of experiments, little C230 enzyme activity in GM120/pAMB12T5S was detected when no inducer was added to growing cells. When the culture was induced with sucrose, C230 was produced at levels superior to those observed in the GM120/pAMB12T5 culture which was likewise induced (FIG. 12). The presence of the sacY positive regulator gene on the pAMB12T5S plasmid positively affected the amount of C230 produced by the *B. subtilis* host cells.

Because of the nature of the promoter that drives expression of xylE in GM120/pA51 and GM120/pA51S, maximal expression requires the use of a host cell which carries the sacU$^h$ mutation (Zukowski et al., supra). In the case of GM120/pAMB12T5 and GM120/pAMB12T5S, however, the T5 synthetic promoter does not require the sacU$^h$ mutation for efficient expression (Zukowski et al., supra), thus host cells which carry the sacU$^h$ mutation are not required. This broadens the choice of host cells which may be used in the application of the inducible expression system described in this invention.

The above results indicate that sacY, when present in multiple copies, stimulates expression of xylE on the same plasmid. Since the xylE gene is considered heterologous for *Bacillus subtilis*, in that it was derived from *Pseudomonas putida*, the inducible expression system of the present system is applicable for controlled expression of foreign genes in Bacillus host microorganisms.

Various other examples and modifications of the foregoing description and examples will be apparent to a person skilled in the art after reading the disclosure without departing from the spirit and scope of the invention, and it is intended that all such example or modifications be included within the scope of the appended claims.

What is claimed is:

1. A plasmid vector for expressing a gene encoding a desired polypeptide in a *B. subtilis* host microorganism, said vector being selected from the group consisting of pA51S and pAMB12T5S.

2. A *B. subtilis* strain transformed with a vector according to claim 1.

3. A *B. subtilis* culture capable of producing a polypeptide by expression of a gene coding therefor, wherein the expression is directed by a plasmid vector according to claim 1.

* * * * *